United States Patent [19]

Welt et al.

[11] Patent Number: 5,565,356
[45] Date of Patent: Oct. 15, 1996

[54] HYBRIDOMA CELL LINES WHICH PRODUCE MONOCLONAL ANTIBODIES HAVING THE PROPERTIES OF MONOCLONAL ANTIBODY 100-310 AND THE MONOCLONAL ANTIBODIES PRODUCED BY THESE HYBRIDOMA CELL LINES

[75] Inventors: Sydney Welt, Armonk; Clarence Williams, Jr., Riverdale; Elsje C. Barendswaard, New York; Chaitanya R. Divgi, New York; Pilar Garin-Chesa, New York; Lloyd J. Old, New York, all of N.Y.

[73] Assignee: Memorial Sloan-Kettering Cancer Center, New York, N.Y.

[21] Appl. No.: 273,277

[22] Filed: Jul. 11, 1994

Related U.S. Application Data

[63] Continuation of Ser. No. 142,550, Oct. 22, 1993, abandoned, which is a continuation of Ser. No. 876,372, Apr. 29, 1992, abandoned.

[51] Int. Cl.$^6$ .............................. C12N 5/20; C07K 16/30
[52] U.S. Cl. .................... 435/240.27; 435/70.21; 435/172.2; 530/387.7; 530/388.8; 530/388.85

[58] Field of Search ...................... 435/70.21, 240.27, 435/172.2; 530/387.1, 387.7, 388.1, 388.8, 388.85

[56] References Cited

FOREIGN PATENT DOCUMENTS 0199141  10/1986  European Pat. Off. ........ C07K 15/00

OTHER PUBLICATIONS

Waldmann Science 252:1657–1622 (1991).
Dillman Annals Internal Medicine 111:592–603 (1989).
Stefel et al. Yalf J Biol Med 57(1984) (Citation Only).
Riker et al. Proc Am Assoc Cancer Res. Ann. Meeting 31(1990).
Welt, et al., J. Clinical Oncology, vol. 8, pp. 1894–1906 (Nov. 1990).

*Primary Examiner*—Christina Y. Chan
*Assistant Examiner*—Phillip Gambel
*Attorney, Agent, or Firm*—Felfe & Lynch

[57] ABSTRACT

Monoclonal antibody 100-310 is found to be reactive against colon cancer cells and would therefore be useful for diagnostic imaging and treatment of colon cancer.

2 Claims, No Drawings

HYBRIDOMA CELL LINES WHICH PRODUCE MONOCLONAL ANTIBODIES HAVING THE PROPERTIES OF MONOCLONAL ANTIBODY 100-310 AND THE MONOCLONAL ANTIBODIES PRODUCED BY THESE HYBRIDOMA CELL LINES

This application is a continuation of Ser. No. 08/142,550, filed on Oct. 22, 1993, now abandoned, which is itself is a continuation of Ser. No. 07/876,372, filed on Apr. 29, 1992, also abandoned.

The invention concerns a hybridoma and monoclonal antibody directed to colon cancer.

SUMMARY OF THE INVENTION

Hybridoma 100-310 and monoclonal antibody produced therefrom (100-310) recognizes colon cancer and normal colon antigen(s).

DESCRIPTION

The widespread occurrence of colon cancer in the U.S. and the west has prompted a search for monoclonal antibodies (mAbs) specific for these colon cancer cells. Monoclonal antibodies capable of distinguishing between normal and cancerous colon cells are useful in diagnosis, prognosis and treatment of this disease. Examination of human cell wastes, exudates and fluids with these antibodies can be used in diagnostic procedures for colon cancer. The monoclonals can be tagged with fluorescent or radioactive tracers for ease in diagnosis.

The Köhler and Milstein technique introduced in 1975 allows production of unlimited quantities of antibody of precise and reproducible specificity. Conventional polyclonal antisera contain a myriad of different antibodies differing in their specificity and properties, whereas a hybridoma produces a single monoclonal antibody with uniform characteristics. The Köhler-Milstein technique starts with the immunization of an animal with subsequent fusion of spleen cells isolated from the immunized animal with an immortal myeloma cell line. These fused cells (hybridomas) grow in culture, and specific clones can be selected producing the mAb of the desired specificity. Each clone produces one specific monoclonal antibody. These hybridomas can, be cultured and/or stored in liquid nitrogen. Thus a constant supply of pure antibody, i.e. monoclonal antibody, is assured.

Antibody proteins recognize specific antigens in an immunological response. Antibody molecules usually recognize a specific region of the antigen known as an epitope or determinant. These antigens can be specific and reside on or in cells and therefore enable specific cells to be recognized by specific antibodies. The cell antigens then operate as cell markers. These markers can be unique for normal and/or cancerous cells. Cell markers can change throughout the normal process of cell differentiation in the normal process or as part of a cell progression to abnormality or cancer. Thus the cell markers provide a cell phenotype.

Monoclonal antibodies to different cell types have been developed. See for example, Old, Lloyd J. et al. (1981) Cancer Res. 41: 361–375, and Eisinger et al. (1982) Proc Nat'l. Acad. Sci. USA 79: 2018.

Since colon cancer is widespread in the West and U.S.A., early diagnosis and treatment is an important medical goal. Diagnosis and treatment of colon cancer can be implemented using monoclonal antibodies specific therefore having fluorescent, nuclear magnetic or radioactive tags. Radioactive genes, toxins and/or drug tagged mAbs can be used for treatment in situ with minimal patient description. Conventional and experimental drugs such as mercaptopurine, methotrexate, adriamycin or any chemotherapeutic agent can be used. Labels such as $^{111}$Indium, $^{99}$Technetium, $^{125}$Iodine or $^{131}$Iodine are used. Toxins such as ricin can be used.

These and more are known to those skilled in the art. See for example Larson, S.M. and Carrasquillo, J. A. in Herberman, R. B. et al. (eds): Immune Response to Metastases, Vol. 2. Boca Raton, Fla., CRC Press 1987, p. 122–126 and Cohn, K. H. et al (1987) Arch. Surg. 122: 1425–1429. These monoclonals can thus be used in lieu of, or in conjunction with, surgery and/or other chemotherapies. U.S. Pat. No. 4,579,827 is directed to some monoclonals for this system as is U.S. Ser. No. 724,991 filed Apr. 19, 1985 hereby incorporated by reference. This latter application concerns mAb A33 (AS33). The EP application number therefore is 199, 141 published in 1986. A hybridoma cell line which produces the nonoclonal antibody A33 was deposited at the American Type Culture Collection, 12301 Parklawn Drive, Rockville, Md. 20852, and has been accorded Accession Number ATCC HB8779. This deposit was made in accordance with the Budapest Treaty, and affords permanence of the deposit and ready access thereto by the public. The deposit was made on Apr. 3, 1985.

The A33 antigen, detected by an IgG2a mouse monoclonal antibody, is expressed in more than 90% of primary or metastatic colon cancers, and in normal colon epithelium. Most ,other normal tissues and tumor types are negative for A33 expression. Because of this restricted expression, A33 can be classified as a differentiation antigen of normal and transformed colonepithelium. Despite considerable effort, the biochemical characterization of A33 is incomplete. The available information suggests that A33 is a heat- and neuraminidase-insensitive, protease-resistant epitope carried by a high molecular-weight glycoprotein. A notable feature of the A33 system is the rapid internalization of the A33 antigen/antibody complex after attachment of mAb A33; over 90% of the attached mAb is internalized within 1–2 minutes. Single-chain constructs of the antibody also elicit this rapid and efficient internalization process.

A phase I imaging trial with $^{131}$I-mAb A33 in patients with hepatic metastases of colorectal cancer has been completed (Welt, S. et al. J. Clin. Oncology 8: 1894–1906 (1990) hereby incorporated by reference). Tumor imaging of metastatic lesions was observed in 19 of the 20 patients. Five to seven days following antibody injection, the tumor: blood ratios ranged from 4:1 to 25:1, the tumor: liver ratios from 7:1 to 100:1, and the % injected dose/gram of tumor up to 0.015%. A comparison of these results with mAb A33 to past clinical tests with mAbs to CEA and 72.3 (the two other antigenic systems that have been most extensively studied) indicates the considerable potential of the A33 system for tumor imaging and therapy.

A phase I therapy trial with escalating doses of $^{131}$I-mAb A33 is now ongoing and after completion will be followed by a phase I trial with $^{125}$I-mAb A33.

Thus these monoclonals reactive with colon cancer have considerable potential to be very useful as part of a chemotherapeutic arsenal against colon cancer. It is therefore important to produce more monoclonals having the same or even higher specificity as an A33. Thus one or more of these can be site-directed to the primary or metastatic tumor for imaging diagnosis and/or treatment.

Mindful of the above, we have prepared a new monoclonal antibody 100-310 which is also very active against colon cancer and reacts against a different antigen, determinant or epitope than A33.

Monoclonal antibody 100-310 is a murine IgG2b reactive with over 90% of colon carcinomas and a small fraction of gastric cancers. Normal colon epithelium also expresses the antigen; thus far, other normal tissues are negative. MAb 100-310 tissue reactivity is similar to the specificity pattern of mAb A33 (Welt, S. et al. Supra). Binding studies using $^{125}$I-mAb 100-310 demonstrate that colon cancer cell lines such as COLO 205 and SW1222 express up to $8\times10^5$ epitopes per cell; binding of $^{125}$I-mAb 100-310 is not blocked by excess cold mAb A33. $^{125}$I-mAb 100-310 is rapidly internalized into the cell, based on acid wash experiments. Radioimmuno-scintigraphy studies demonstrate that the $^{125}$I-mAb localizes to transplanted SW1222 in nu/nu mice with tumor: nontumor ratios of 40:1 on day 4, with 35% accumulation of the injected dose/gram. Thus 100-310 is useful for diagnosis and treatment of colon cancer. Based on these preliminary results, clinical trials are planned.

Unlike all other mAbs detecting pan-carcinoma antigens, our colon-specific mAbs (A33 and 100-310) can be used to diagnose tumors as colon cancer in vitro and in vivo. No false-positive scans have been observed in more than 50 patients imaged with mAb A33. In addition, as these antibodies localize specifically to colon cancer and normal colon cells, they can be used to treat diseases of the colon (e.g., polyposis coli, ulcerative colitis, and colon cancer) in which genetic defects are present in both normal and malignant cells. As these antibodies are internalized by the cells, they can deliver drugs, genes, toxins, or even radioisotopes directly to the cytoplasm. For example, $^{125}$Iodine is much more cytotoxic to cells in the cytoplasm than outside the cell. The internalization characteristic of these antibodies adds specificity to the cytotoxic agents. No other antibody has this specificity and allows access to the intracellular compartment.

EXAMPLE

Immunization

Monoclonal antibody 100-310 was generated by immunizing BALB/c mice sequentially with human colon carcinoma cell lines SW1222 and COLO 205 and human pancreas carcinoma cell line ASPC-1.

After immunization with each of the three cell lines, B cells from the spleen were fused with SP/20 myeloma cells. The hybridoma supernatants were screened against a panel of A33 antigen-positive and A33 antigen-negative cell lines by the hemagglutination assay. Monoclonal antibody 100-310 was selected because the cell line's reactivity was similar to that of mAb A33. However, blocking experiments clearly demonstrate that mAb 100-310 binds to a novel determinant that is different from A33. Immunostaining of human tissues shows mAb 100-310 to be organ-specific, that it binds only to normal colon cells and to tumors derived from the colon. Cell line specificity of 100-310 is detailed below:

| Monoclonal Antibody 100-310, Human Cell Line Specificity Analysis: | |
|---|---|
| Colon Cancer: | |
| positive- | SW1222, COLO 205, SW403, LS180. |
| negative- | HT29, SW1116, SW48, SW480, Caco-2, SW620, HCT15, SW837, COLO 201, DLD-1, HCT-116 LoVo, SW1417, SK-CO-10, SK-CO-17, SW1463, SK-CO-1 (+/−), LS 174T (weak). |
| Pancreas Cancer: | |
| positive- | ASPC-1 |
| negative- | Bx PC-3, Capan-1-, Capan-2. |
| Renal Cancer: | |
| negative- | SK-RC-44, SK-RC-45, SK-RC-48, SK-RC-17, SK-RC-38, SK-RC-9, SK-RC-1, SK-RC-18, SK-RC-39, SK-RC-39, SK-RC-29, SK-RC-8, SK-RC-7. |
| Melanoma: | |
| negative- | SK-MEL-37, SK-MEL-93-2, SK-MEL-30, SK-MEL-31, SK-MEL-23, SK-MEL-19, SK-MEL-170, SK-MEL-28, SK-MEL-41. |
| Ovarian Cancer: | |
| negative- | SK-OV-3, SK-OV-6. |
| Lung Cancer: | |
| negative- | CaLu-3, CaLu-6, SK-LU-8. |
| Breast Cancer: | |
| negative- | Mcf7, BT-20, SK-BR-3. |

Tissue specificity analysis is detailed below:

| Monoclonal Antibody 100-310 Human Tissue Specificity Analysis: | |
|---|---|
| Normal Tissues | |
| positive- | colonic epithelium (6) |
| negative- | bladder (2) |
| | spleen (3) |
| | lung (5) |
| | ovary (2) |
| | adrenal (2) |
| | stomach (2) |
| | esophagus (2) |
| | pancreas (2) |
| | testes (2) |
| | breast (2) |
| | liver (2) |
| | skin (1) |
| Cancers | |
| positive- | colon cancer (19) |
| negative- | colon cancer (1) |
| | breast cancer (2) |
| | renal cancer (6) |
| | lung cancer (4) |
| | ovarian cancer (2) |
| | pancreas cancer (1) |

( ) = number of cases tested

Thus, 95% colon cancers react to A33 and 100-310. Generally, if the cancer is negative to A33, it is negative to 100-310. However, the 100-310 antibody reacts with a different antigen, epitope or determinant than A33 since 100-310 does not block mAb A33 binding.

Thus the 100-310 antibody can be used for better colon cancer imaging and treatment since different antigenic entities of the cancer are attacked. Different antigenic fragments of 100-310 can be used such as Fab or as well. We especially will find 100-310 useful to seek out and attack metastases bearing the colon carcinoma marker antigen.

This then would be useful e.g. to prepare with different tags as treatments and to potentiate treatments for colon cancer and ensure determination or removal thereof.

The 100-310 hybridoma is on deposit at the Ludwig Institute for Cancer Research, New York Branch at Memorial Sloan Kettering Cancer Center, 1275 York Avenue, New York, N.Y., 10021. The cell line has been placed on deposit at the American Type Culture Collection, 1230 Parklawn Drive, Rockville, Md., 20852 on Apr. 28, 1992 under the ATCC designation HB 11028.

It will be understood that the specification and examples illustrate but do not limit the present invention other embodiments within the spirit and scope of the invention will suggest themselves to those skilled in the art.

We claim:

1. Hybridoma cell line ATCC HB 11028 which produces a monoclonal antibody which binds to an antigen bound by the monoclonal antibody produced by hybridoma cell line ATCC HB 8779, but to a different epitope.

2. Monoclonal antibody produced by the hybridoma cell line ATCC HB 11028 of claim 1.

* * * * *

UNITED STATES PATENT AND TRADEMARK OFFICE
CERTIFICATE OF CORRECTION

PATENT NO. : 5,565,356
DATED : October 15, 1996
INVENTOR(S) : Welt et al.

It is certified that error appears in the above-identified patent and that said Letters Patent is hereby corrected as shown below:

On the cover page, in the section titled Reference Cited, Other Publications, line 3, change "Yalf" to -- Yale --.

In column 1, line 45, after "can" delete -- , --.

In Column 2, line 21, change "nonoclonal" to -- monoclonal --.

In column 2, line 31, after "Most" delete -- , --.

Signed and Sealed this

Twenty-seventh Day of February, 2001

Attest:

NICHOLAS P. GODICI

Attesting Officer

Acting Director of the United States Patent and Trademark Office